United States Patent
Russ

(10) Patent No.: US 9,918,803 B2
(45) Date of Patent: Mar. 20, 2018

(54) COMPLIANCE-BASED CLEANING DEVICE, SYSTEM AND METHOD

(71) Applicant: JONNAT MANAGEMENT CORP., Massapequa, NY (US)

(72) Inventor: Jay Russ, Massapequa, NY (US)

(73) Assignee: JONNAT MANAGEMENT CORP, Massapequa, NY (US)

(*) Notice: Subject to any disclaimer, the term of this patent is extended or adjusted under 35 U.S.C. 154(b) by 327 days.

(21) Appl. No.: 14/659,891

(22) Filed: Mar. 17, 2015

(65) Prior Publication Data

US 2016/0271659 A1  Sep. 22, 2016

(51) Int. Cl.

| A61B 90/70 | (2016.01) |
|---|---|
| A61B 7/00 | (2006.01) |
| A61L 2/00 | (2006.01) |
| A61L 2/10 | (2006.01) |
| A61L 2/18 | (2006.01) |
| A61L 2/22 | (2006.01) |
| A61L 2/24 | (2006.01) |
| A61B 5/00 | (2006.01) |

(52) U.S. Cl.
CPC ............ *A61B 90/70* (2016.02); *A61B 7/00* (2013.01); *A61L 2/00* (2013.01); *A61L 2/10* (2013.01); *A61L 2/18* (2013.01); *A61L 2/186* (2013.01); *A61L 2/22* (2013.01); *A61L 2/24* (2013.01); *A61B 5/4833* (2013.01); *A61L 2202/14* (2013.01); *A61L 2202/24* (2013.01)

(58) Field of Classification Search
None
See application file for complete search history.

(56) References Cited

U.S. PATENT DOCUMENTS

| 7,503,335 | B2* | 3/2009 | Perlman | A61B 90/70 134/166 C |
|---|---|---|---|---|
| 2011/0197921 | A1* | 8/2011 | Rubin | A61L 2/28 134/18 |
| 2013/0268293 | A1* | 10/2013 | Knudson | G06Q 50/22 705/2 |

* cited by examiner

*Primary Examiner* — Eric W Golightly
(74) *Attorney, Agent, or Firm* — F. Chau & Associates, LLC

(57) ABSTRACT

A compliance-based cleaning device includes a receiving area configured to receive a piece of equipment to be cleaned, a cleaning member located in proximity to the receiving area and configured to perform a cleaning process on the piece of equipment, a compliance component configured to monitor the cleaning process performed on the piece of equipment, and a network component configured to transmit compliance data to a compliance database in response to the cleaning member performing the cleaning process on the piece of equipment. The compliance data includes identifying information obtained by the compliance component.

14 Claims, 7 Drawing Sheets

COMPLIANCE-BASED CLEANING DEVICE, SYSTEM AND METHOD

BACKGROUND

1. Technical Field

Exemplary embodiments of the present invention relate to compliance-based cleaning of equipment, and more particularly, to a device, system and method of compliance-based cleaning of equipment.

2. Discussion of Related Art

There are many environments in which it is desirable to clean (e.g., disinfect and/or sterilize) tools or equipment. For example, in a medical environment such as a doctor's office, hospital, ambulatory surgery center, nursing facility, rehabilitation facility, etc., it is necessary to clean equipment to prevent the spread of germs, bacteria, viruses, fungus, etc., and to guard against, limit or prevent hospital or facility acquired infection.

Recent studies have suggested that during a patient examination, the chestpiece of a medical practitioner's (e.g., a doctor, nurse, physician's assistant, etc.) stethoscope, which is the portion that comes into contact with a patient's skin, typically acquires more germs, bacteria, viruses and fungus than any part of the medical practitioner's hand other than his or her fingertips. As a result, using the same stethoscope on different patients without cleaning the stethoscope between examinations poses a serious risk of spreading germs, bacteria, viruses, fungus, etc., and causing hospital or facility acquired infection.

In an effort to guard against, limit or prevent the spreading of germs, bacteria, viruses, fungus, etc. between patients, disposable stethoscope covers (e.g., cloth or barrier film covers) are sometimes used on the chestpiece of a stethoscope between examinations. However, the use of a stethoscope cover may actually result in the introduction of additional bacteria through the covers, and also may negatively impact the functionality of the stethoscope. Moreover, the ability of a medical practitioner to perform an effective examination with the stethoscope, despite the impaired or reduced functionality of the stethoscope as a result of covering the chestpiece, is extremely variable and is affected by the practitioner's skill, experience, and hearing, which may in turn be affected by aging related changes. Adverse consequences from covering the stethoscope, coupled with increased legal liability risk attendant thereto, suggest that covering the stethoscope is a poor substitute for cleaning it in a fashion which can be verified and documented. In addition, medical practitioners frequently forget or neglect to use or change covers, and may feel a false sense of safety through use of the covers, resulting in the stethoscopes being cleaned less frequently.

Finally, most if not all manufacturers of stethoscopes warn against covering the chestpiece when in use. Regularly cleaning the chestpiece of a stethoscope between all patient examinations is typically thought to be the most efficient way to guard against, limit or prevent the spreading of germs, bacteria, viruses, funguses, etc. However, medical practitioners frequently forget or neglect to perform this cleaning, regardless of whether stethoscope covers are being utilized. Given the risk of hospital or facility acquired infection, some medical practitioners opt to forego the stethoscope examination entirely. Even when they have the means to clean the stethoscope, medical practitioners often find that those means are not conveniently placed at or near the hand hygiene dispenser.

SUMMARY

According to an exemplary embodiment of the present invention, a compliance-based cleaning device includes a receiving area configured to receive a piece of equipment to be cleaned, a cleaning member located in proximity to the receiving area and configured to perform a cleaning process on the piece of equipment, a compliance component configured to monitor the cleaning process performed on the piece of equipment, and a network component configured to transmit compliance data to a compliance database in response to the cleaning member performing the cleaning process on the piece of equipment. The compliance data includes identifying information obtained by the compliance component.

In an exemplary embodiment, the identifying information includes first identifying information that identifies the piece of equipment, second identifying information that identifies the compliance-based cleaning device, third identifying information that identifies a user that performed the cleaning process on the piece of equipment using the compliance-based cleaning device, and/or fourth identifying information that indicates whether the user performed a hand sanitization cleaning process at substantially a same time that the cleaning process is performed on the piece of equipment.

In an exemplary embodiment, the compliance component includes a camera configured to capture a readable indicia disposed on the piece of equipment. The readable indicia uniquely identifies the piece of equipment. The readable indicia may include at least one of a serial number, a registration number, and a barcode.

In an exemplary embodiment, the compliance component includes a radio-frequency identification (RFID) reader configured to capture a readable indicia disposed on the piece of equipment. The readable indicia is an RFID tag that uniquely identifies the piece of equipment.

In an exemplary embodiment, the cleaning process includes disinfecting the piece of equipment.

In an exemplary embodiment, the cleaning process includes sterilizing the piece of equipment.

In an exemplary embodiment, the compliance-based cleaning device further includes a cleaning solution chamber connected to the cleaning member and configured to store a liquid cleaning solution and provide the liquid cleaning solution to the cleaning member. The cleaning process is performed on the piece of equipment using the liquid cleaning solution.

In an exemplary embodiment, the cleaning member includes a plurality of holes, and the liquid cleaning solution is sprayed onto the piece of equipment through the plurality of holes during the cleaning process.

In an exemplary embodiment, the compliance-based cleaning device further includes a compliance sensor disposed in the receiving area. The compliance sensor is configured to detect insertion of the piece of equipment in the receiving area.

In an exemplary embodiment, the cleaning process is automatically started upon the compliance sensor detecting insertion of the piece of equipment in the receiving area.

In an exemplary embodiment, the compliance component is a camera configured to capture an image of a user performing the cleaning process, and the image is included in the compliance data transmitted to the compliance database.

In an exemplary embodiment, the compliance component is at least one of a fingerprint scanner configured to obtain a fingerprint of a user performing the cleaning process, and an identification card scanner configured to obtain identifying indicia of the user via an identification card. At least one of the fingerprint and the identifying indicia is included in the compliance data transmitted to the compliance database.

In an exemplary embodiment, the compliance-based cleaning device further includes a hand sanitizing solution chamber configured to store a hand sanitizing solution, and a hand sanitizing component connected to the hand sanitizing solution chamber and configured to sanitize a hand of a user performing the cleaning process. The identifying information indicates whether the user performed a hand sanitization cleaning process at substantially a same time as the cleaning process is performed on the piece of equipment.

In an exemplary embodiment, the piece of equipment to be cleaned is a chestpiece of a stethoscope.

According to an exemplary embodiment of the present invention, a method of compliance-based cleaning includes receiving a piece of equipment to be cleaned in a compliance-based cleaning device, performing a cleaning process on the piece of equipment upon receiving the piece of equipment in the compliance-based cleaning device, monitoring the cleaning process performed on the piece of equipment, and transmitting compliance data from the compliance-based cleaning device to a compliance database in response to performing the cleaning process on the piece of equipment. The compliance data includes identifying information obtained during the cleaning process.

In an exemplary embodiment, the identifying information includes first identifying information that identifies the piece of equipment, second identifying information that identifies the compliance-based cleaning device, and third identifying information that identifies a user that performed the cleaning process on the piece of equipment using the compliance-based cleaning device.

BRIEF DESCRIPTION OF THE DRAWINGS

The above and other features of the present invention will become more apparent by describing in detail exemplary embodiments thereof with reference to the accompanying drawings, in which.

DETAILED DESCRIPTION OF THE EXEMPLARY EMBODIMENTS

Figure 1A:
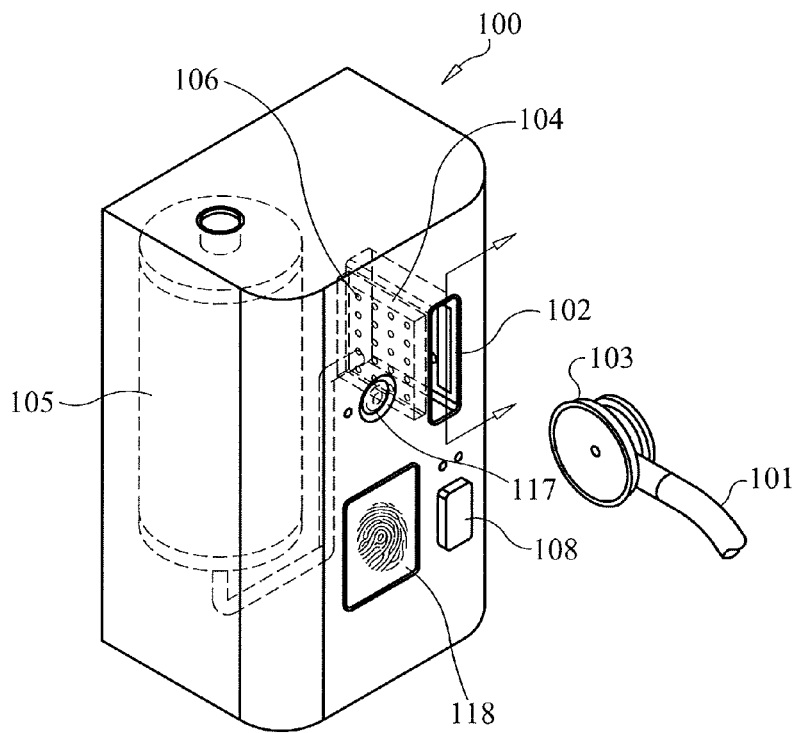
FIGS. 1A-1B show a compliance-based cleaning device according to an exemplary embodiment of the present invention.

Exemplary embodiments of the present invention will be described more fully hereinafter with reference to the accompanying drawings. Like reference numerals may refer to like elements throughout the accompanying drawings. It will be understood that elements shown in the drawings may not be drawn to scale, and the size of elements in the drawings may be exaggerated for clarity.

Exemplary embodiments of the present invention provide a system and device for implementing compliance-based cleaning. Herein, the term cleaning may refer to disinfecting and/or sterilizing.

For convenience of explanation, exemplary embodiments of the present invention are described herein with reference to a compliance-based cleaning device, system and method to clean a stethoscope in a medical setting (e.g., a hospital, ambulatory surgery center, nursing facility, rehabilitation facility, doctor's office, operation room, intensive care unit (ICU), emergency room, medical center, etc.). However, it is to be understood that utilization of the compliance-based cleaning device, system and method with a stethoscope is merely exemplary. That is, the compliance-based cleaning device, system and method according to exemplary embodiments is not limited to use with a stethoscope, nor is it limited to a medical setting. For example, exemplary embodiments of the present invention may be applied to any tool/device/equipment that is to be cleaned, and that is capable of being identified by a readable indicia such as, for example, a serial number, a registration number, a barcode, an NFC tag, etc., in which the readable indicia stores/includes a unique identifier capable of uniquely identifying the tool/device/equipment. For example, it is to be understood that when a chestpiece of a stethoscope is herein described as undergoing a cleaning process, the cleaning process may be performed on the targeted portion of any other piece of equipment (or the entire piece of equipment) being cleaned in accordance with exemplary embodiments of the present invention. Further, it is to be understood that the readable indicia may form the basis for a database of such tool/device/equipment such as, for example, by the medical practitioner registering the readable indicia of the stethoscope with the hospital, facility or office, so that the stethoscope is identifiable as the stethoscope utilized by the specific medical practitioner, as described in further detail below.

Further, it is to be understood that exemplary embodiments of the present invention may be used in any setting, including non-medical settings. Referring to a medical setting, in addition to stethoscopes, exemplary embodiments may also be utilized with, for example, blood pressure cuffs, hemodialysis machines, X-ray machines, thermometers, hospital pagers, endoscopes, manual ventilation bags, CPR manikins, ultrasound instruments, reusable transducer heads, glucometers, and blood pressure machines. It is to be further understood that exemplary embodiments of the present invention do not rely upon the present existence of readable indicia, as readable indicia may be added to tools/devices/equipment such as, for example, the addition of a readable indicia (e.g., a serial or registration number, an NFC tag, etc.) by the manufacturer or the addition of a readable indicia or differentiating mark or symbol by the owner or user. It is to be understood that exemplary embodiments of the present invention may be used in cleaning, disinfection and/or sterilization devices to capture readable identifiers of some or all of the tools/devices/equipment being cleaned, disinfected or sterilized in one or a series of processes. Therefore, the present invention may be added to, or incorporated into, existing cleaning, disinfection and/or sterilization equipment.

Herein, the term medical practitioner refers to any person providing medical services to a patient including, for example, a doctor, nurse, physician's assistant, etc. The term user refers to any person using a compliance-based cleaning device or system according to exemplary embodiments of the present invention, including a medical practitioner in a medical setting or a non-medical practitioner in a non-medical setting.

Figure 1B:
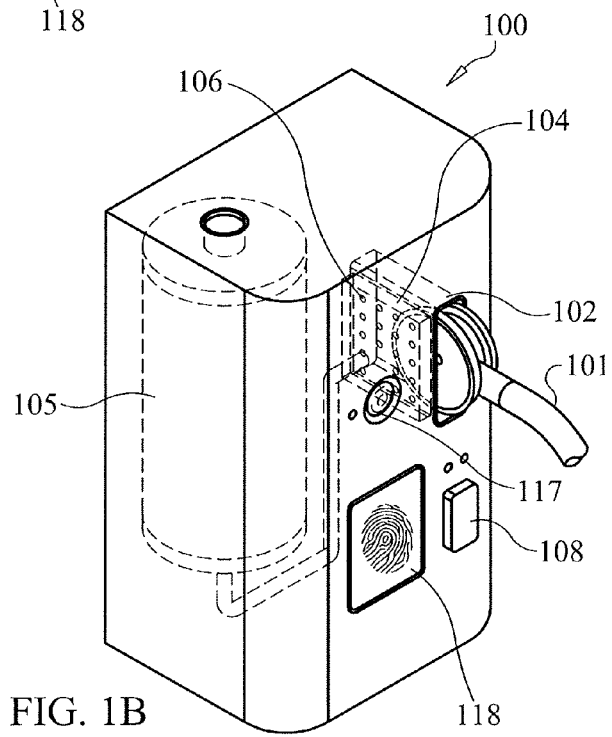
Figure 1C:
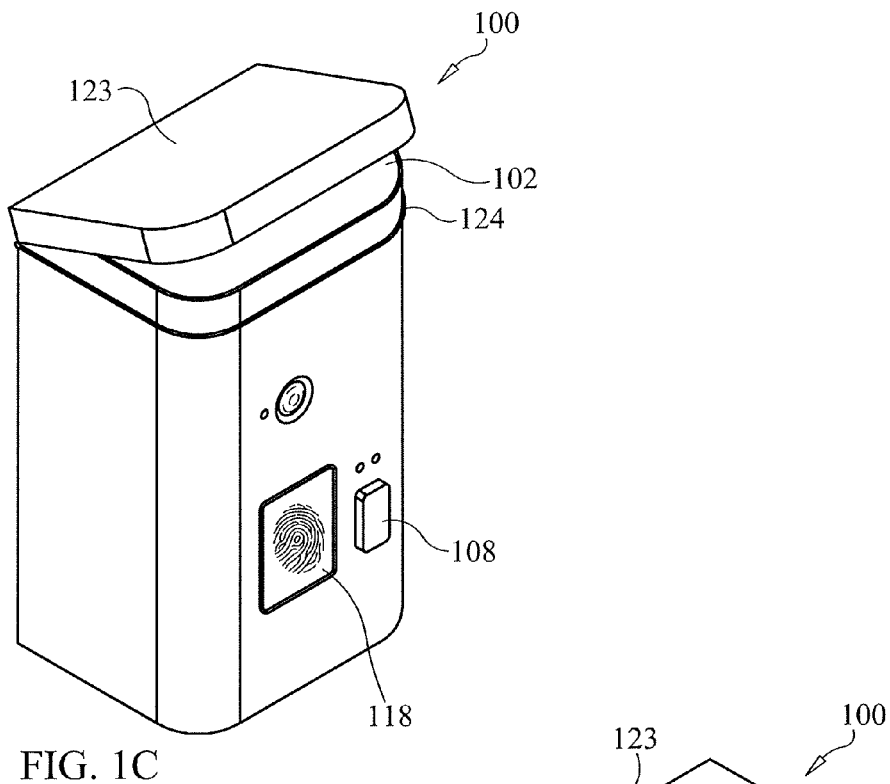
FIGS. 1C-1D show a compliance-based cleaning device according to an exemplary embodiment of the present invention.
Figure 1D:
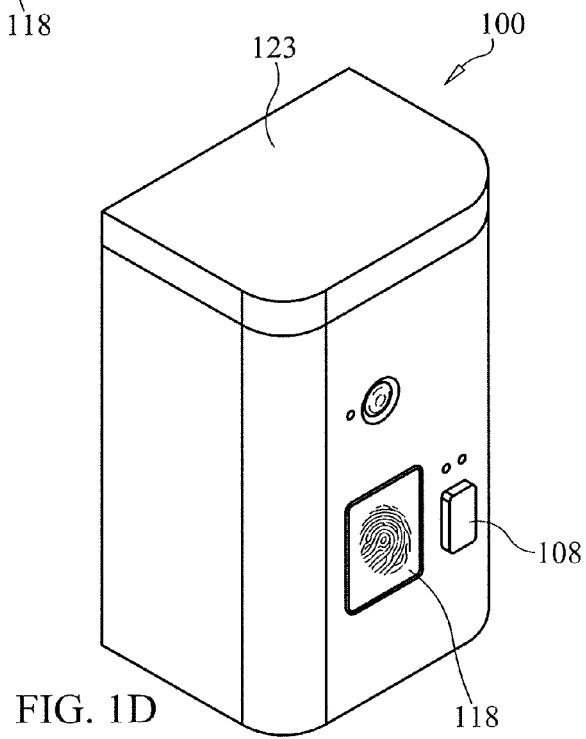
Figure 2A:
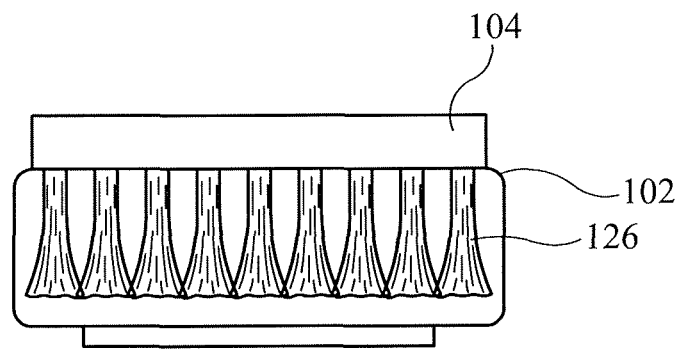
FIGS. 2A-2C show a receiving area and a cleaning member of a compliance-based cleaning device according to exemplary embodiments of the present invention.
Figure 2B:
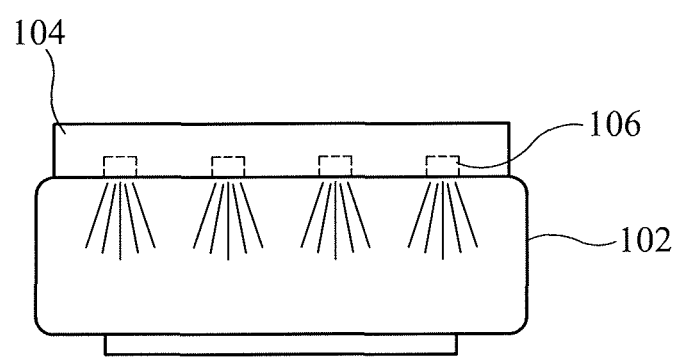
Figure 2C:
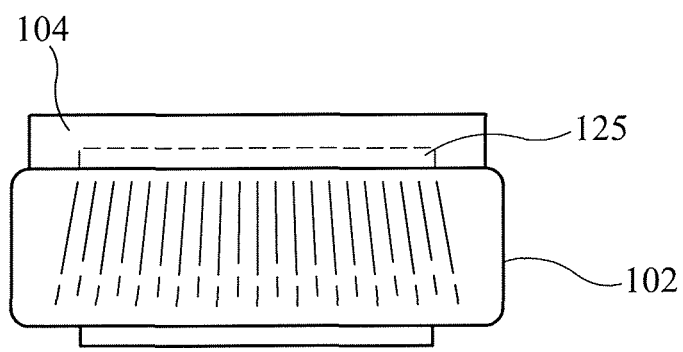
Figure 5:
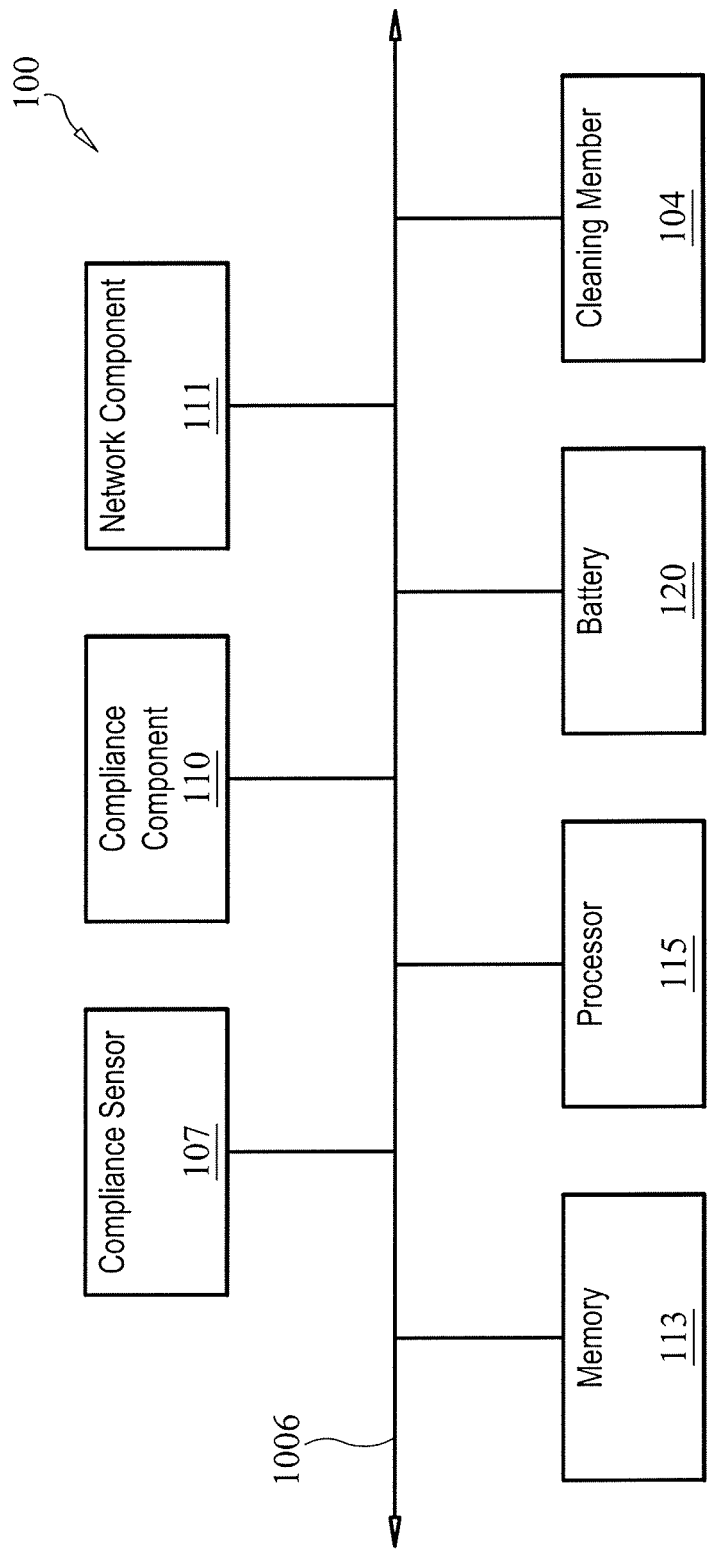
FIG. 5 is a block diagram illustrating a compliance-based cleaning device according to an exemplary embodiment of the present invention.

FIGS. 1A-1B show a compliance-based cleaning device according to an exemplary embodiment of the present invention. FIGS. 1C-1D show a compliance-based cleaning device according to an exemplary embodiment of the present invention. FIG. 2A shows a receiving area and a cleaning member of a compliance-based cleaning device in which the cleaning member is implemented using a plurality of brushes according to an exemplary embodiment of the present invention. FIG. 2B shows a receiving area and a cleaning member of a compliance-based cleaning device in which the cleaning member is implemented using a plurality of holes through which a liquid cleaning solution is sprayed according to an exemplary embodiment of the present invention. FIG. 2C shows a receiving area and a cleaning member of a compliance-based cleaning device in which the cleaning member is implemented using an ultraviolet lamp that produces ultraviolet light according to an exemplary embodiment of the present invention. FIG. 5 is a block diagram illustrating a compliance-based cleaning device according to an exemplary embodiment of the present invention The compliance-based cleaning device 100 of FIGS. 1A-1B is configured to receive a portion of a stethoscope 101. For example, the compliance-based cleaning device 100 may include a receiving area 102 shaped and dimensioned to receive the chestpiece 103 of the stethoscope 101. The chestpiece 103 includes the bell and the diaphragm of the stethoscope 101. The chestpiece 103 of the stethoscope 101 may also be referred to herein as the head of the stethoscope 101. The receiving area 102 is shaped and dimensioned to receive a standard size chestpiece 103. For example, most commonly used stethoscopes, including both stethoscopes commonly used for infants and adults, have a diameter between about 1 inch and about 3 inches. Accordingly, the receiving area 102 of the compliance-based cleaning device 100 may include an opening in which the chestpiece 103 is inserted that has a diameter in the range of about 1 inch to about 3 inches or greater. According to an exemplary embodiment, the opening of the receiving area 102 may be about 3 inches or greater, which permits the compliance-based cleaning device 100 to be used with a variety of stethoscopes having differently sized chestpieces. Alternatively, in an exemplary embodiment, the opening of the receiving area 102 may be designed to receive a chestpiece 103 having a specific size such as, for example, a chestpiece having a diameter of about 1.7 inches.

It is to be understood that the receiving area 102 according to exemplary embodiments designed to receive equipment other than the chestpiece 103 of a stethoscope 101 is shaped and dimensioned to receive the piece of equipment to be cleaned. That is, the receiving area 102 is not limited to the size and shape shown in the exemplary embodiment of FIGS. 1A and 1B. For example, it is to be understood that exemplary embodiments are not limited to the slot-shaped receiving area 102 that is shaped and dimensioned to receive primarily the chestpiece 103 of a stethoscope 101, as illustrated in FIGS. 1A-1B. For example, as shown in FIGS. 1C-1D, in an exemplary embodiment, instead of a slot-shaped receiving area 102, the compliance-based cleaning device 100 may include a cavity as the receiving area 102. The cavity-based receiving area 102 may be larger than the slot-shaped receiving area 102. As shown in FIGS. 1C-1D, the receiving area 102 may be accessed via a lid 123 disposed, for example, at an upper portion of the compliance-based cleaning device 100. A seal 124 may be utilized with the lid 123 to create a sealed coupling between the compliance-based cleaning device 100 and the lid 123. For example, the piece of equipment to be cleaned may be entirely placed within the receiving area 102, the lid 123 may be closed to seal the receiving area 102, and the cleaning process may then be performed on the piece of equipment.

Due to the large size and the shape of the receiving area 102 in an exemplary embodiment according to FIGS. 1C-1D, a single compliance-based cleaning device 100 may be utilized to clean a variety of pieces of equipment. For example, a single compliance-based cleaning device 100 may be used to clean stethoscopes, blood pressure cuffs, thermometers, hospital pagers, endoscopes, etc. It is to be understood that, other than the shape, size and structure of the receiving area 102, all or some of the components and capabilities of the compliance-based cleaning device 100 shown in and described with reference to FIGS. 1A-1B (as well as FIG. 1E) may also be included in the compliance-based cleaning device 100 of FIGS. 1C-1D.

Referring again to FIGS. 1A-1B, since the chestpiece 103 of the stethoscope 101 is the portion of the stethoscope 101 that typically comes into direct contact with a large number of patients, the chestpiece 103 typically includes the largest amount of germs, bacteria, viruses, fungus, etc. relative to the rest of the stethoscope 101. Thus, the chestpiece 103 is the portion of the stethoscope 101 for which cleaning is most important. According to the exemplary embodiment shown in FIGS. 1A-1B, the receiving area 102 of the compliance-based cleaning device 100 is shaped and dimensioned to receive primarily the chestpiece 103 of the stethoscope 101. For example, the receiving area 102 is not shaped and dimensioned to receive the earpieces and/or the tubing of the stethoscope 101 (although a small amount of the tubing near the chestpiece 103 may enter the receiving the area 102 along with the chestpiece 103). This configuration allows for the chestpiece 103 to be adequately cleaned without potentially damaging the tubing and/or the earpieces of the stethoscope 101 as the result of unneeded cleaning of these components. Alternatively, according to exemplary embodiments, the entire stethoscope 101 may be placed within the receiving area 102 (see, for example, FIGS. 1C-1D).

According to an exemplary embodiment of the present invention, the compliance-based cleaning device 100 performs a cleaning process using a liquid cleaning solution. Herein, the term cleaning process refers to the period in which the piece of equipment being cleaned (e.g., the chestpiece 103 of the stethoscope 101) is disposed within the receiving area 102 of the compliance-based cleaning device 100 and is being cleaned by, for example, being exposed to the liquid cleaning solution or ultraviolet rays, as described below. In addition, exemplary embodiments may utilize a brush or a plurality of brushes 126 (see FIG. 2A) or other surface for physically wiping the piece of equipment being cleaned. These cleaning processes may be separately implemented or combined into a single compliance-based cleaning device 100.

Exemplary embodiments in which the cleaning process is performed using a liquid cleaning solution are described herein.

The duration of the cleaning process may vary according to exemplary embodiments of the present invention. For example, in an exemplary embodiment, the duration of the cleaning process may be between about 30 seconds and about 60 seconds, resulting in a significant reduction of microbial population on the chestpiece 103. In other exemplary embodiments, the cleaning process may be shorter (e.g., less than about 30 seconds) or longer (e.g., up to about 2 minutes or longer). The compliance-based cleaning device 100 may include a cleaning member 104 and a cleaning solution chamber 105. The cleaning member 104 is connected to the cleaning solution chamber 105. The cleaning solution chamber 105 stores a liquid cleaning solution used to clean the piece of equipment (e.g., the chestpiece 103 of the stethoscope 101) once the piece of equipment (e.g., the chestpiece 103) has been inserted into the receiving area 102 of the compliance-based cleaning device 100. For example, once the piece of equipment to be cleaned (e.g., the chestpiece 103) has been inserted into the receiving area 102, the liquid cleaning solution is passed from the cleaning solution chamber 105 to the cleaning member 104, and the cleaning process is performed.

The liquid cleaning solution may be any type of solution capable of cleaning the piece of equipment. For example, the cleaning solution may include, but is not limited to, a germicidal compound, hydrogen peroxide, peracetic acid, alcohols (e.g., ethyl alcohol, isopropyl alcohol (e.g., about 70% to about 90% isopropyl alcohol), methyl alcohol, etc.), chlorine and chlorine compounds, formaldehyde, glutaraldehyde, ortho-phthalaldehyde, iodophors, phenolics, quaternary ammonium compounds, or a combination thereof. Alternatively, exemplary embodiments may use means other than a liquid cleaning solution to clean the piece of equipment (e.g., the chestpiece 103), such as, for example, an ultraviolet light (see FIG. 2C) and/or a brush 126 (see FIG. 2A).

The cleaning solution chamber 105 passes the liquid cleaning solution stored therein to the cleaning member 104. The cleaning member 104 is located in proximity to the receiving area 102 of the compliance-based cleaning device 100. For example, the cleaning member 104 may be located within the receiving area 102 or adjacent to the receiving area 102. The cleaning member 104 may include, for example, a plurality of holes 106, as shown in FIG. 2B. The liquid cleaning solution may be sprayed onto the piece of equipment (e.g., the chestpiece 103) through the plurality of holes 106 to clean the piece of equipment (e.g., the chestpiece 103). For example, a mist formed from the liquid cleaning solution may be sprayed onto the chestpiece 103 through the plurality of holes 106 to clean the chestpiece 103. Utilization of the plurality of holes 106 allows for the chestpiece 103 to be cleaned without submerging the chestpiece 103 in the cleaning solution, thus, permitting the chestpiece 103 to be cleaned without being damaged.

Exemplary embodiments in which the cleaning process is performed using ultraviolet light are described herein.

According to an exemplary embodiment of the present invention, the cleaning device 100 performs a cleaning process using ultraviolet light. For example, exemplary embodiments utilize ultraviolet germicidal irradiation (UVGI) to clean the piece of equipment (e.g., the chestpiece 103 of the stethoscope 101). In embodiments that perform the cleaning process using ultraviolet light, the cleaning member 104 includes a germicidal ultraviolet lamp 125 (see FIG. 2C) that irradiates the piece of equipment (e.g., the chestpiece 103) with ultraviolet light at a short enough wavelength to kill or inactivate microorganisms present on the chestpiece 103. Exemplary embodiments that perform the cleaning process using ultraviolet light may not include the cleaning solution chamber 105.

According to exemplary embodiments of the present invention, the compliance-based cleaning device 100 may include a first cleaning member 104 including the plurality of holes 106 and the cleaning solution chamber 105 to implement a first cleaning process utilizing a liquid cleaning solution, as well as a second cleaning member 104 (e.g., a germicidal ultraviolet lamp) to implement a second cleaning process utilizing ultraviolet light. The compliance-based cleaning device 100 may allow a user to select one of the first and second cleaning methods to perform, or both of the first and second cleaning methods.

A compliance sensor 107 (e.g., a chestpiece sensor) may be disposed within the receiving area 102 of the compliance-based cleaning device 100. The compliance sensor 107 detects insertion of the piece of equipment (e.g., the chestpiece 103) into the receiving area 102, which allows for the cleaning process to automatically occur upon the chestpiece 103 being inserted into the receiving area 102. Alternatively, the cleaning process may be started manually by the medical practitioner by, for example, pressing a button, lever, switch, etc.

The compliance sensor 107 may be, for example, a proximity sensor that detects the presence of the piece of equipment (e.g., the chestpiece 103) in the receiving area 102 without physically contacting the chestpiece 103. The proximity sensor may be, for example, an inductive sensor, a capacitive sensor, a photoelectric sensor such as an infrared sensor, a through-beam sensor, a retro-reflective sensor, a diffuse sensor, or an ultrasonic sensor. Alternatively, the compliance sensor 107 may be, for example, a physical sensor that detects the presence of the chestpiece 103 in the receiving area 102 via establishing physical contact with the chestpiece 103 (e.g., a switch that is activated upon the chestpiece 103 pressing/depressing the switch). Alternatively, the cleaning device 100 may include a user input 108 (e.g., a button, switch, lever, etc.) allowing the user to manually begin the cleaning process. Exemplary embodiments may include both the compliance sensor 107 and the user input 108, or one of the compliance sensor 107 and the user input 108.

According to exemplary embodiments, the duration of the cleaning process may be, for example, a pre-set amount of time or a user-defined amount of time, or the cleaning process may be performed for the entire amount of time that the piece of equipment (e.g., the chestpiece 103) is detected as being disposed within the receiving area 102 of the compliance-based cleaning device 100. According to exemplary embodiments, the cleaning process may be performed a single time (e.g., the chestpiece 103 may be continuously sprayed with the liquid cleaning solution, or irradiated with ultraviolet light, for a pre-set number of seconds or for the entire time that the chestpiece 103 is disposed within the receiving area 102) or multiple times (e.g., the chestpiece 103 may be sprayed once every first pre-set n196umber of seconds, or irradiated with ultraviolet light every first pre-set number of seconds, for a total duration of a second pre-set number of seconds).

The compliance-based cleaning device 100 includes a compliance component 110. The compliance component 110 may be, for example, a camera, or a radio-frequency identification (RFID) reader such as, for example, a near field communication (NFC), as described in further detail below. The compliance component 110 allows for the monitoring of the cleaning processes performed by the compliance-based cleaning device 100. For example, the compliance component 110 allows for the tracking and recording of cleaning processes relative to a specific piece of equipment (e.g., a specific stethoscope 101). For example, every time a cleaning process is performed on a stethoscope 101 by the compliance-based cleaning device 100, the compliance component 110 monitors the cleaning process and obtains identifying information (e.g., information included in, for example, readable indicia disposed on the stethoscope 101, as described below). Once the identifying information has been obtained, compliance data (e.g., cleaning process records) based on the identifying information may be created and transmitted from the compliance-based cleaning device 100 to a compliance database 1000 via, for example, a network component 111 of the compliance-based cleaning device 100. The network component 111 may be, for example, a wired network component (e.g., an Ethernet interface) or a wireless network component (e.g., a WiFi transceiver, a cellular transceiver, etc.). The compliance component 110 may be implemented in a variety of manners and may include a plurality of sub-components (e.g., multiple cameras, scanners, etc.) as described in further detail below. The compliance component 110 may be placed at a variety of locations in proximity with the receiving area 102 based on the type of equipment being cleaned and the expected location of readable indicia on the piece of equipment being cleaned relative to the receiving area 102.

Figure 3:
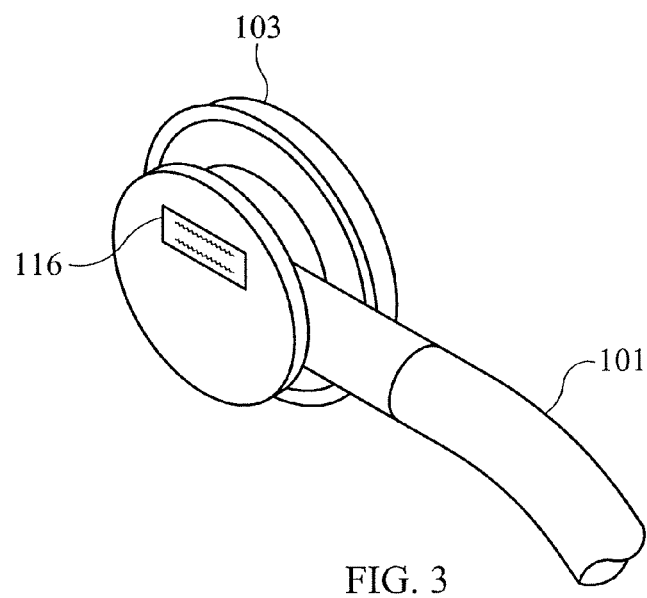
FIG. 3 shows a stethoscope including readable indicia used by a compliance-based cleaning device to identify the stethoscope according to an exemplary embodiment of the present invention.

In an exemplary embodiment, the compliance component 110 includes a camera. The camera is utilized to capture readable indicia 116 (see FIG. 3) disposed on the stethoscope 101. As described above, the readable indicia 116 may be, for example, a serial number, a registration number, a barcode, etc. that is disposed on the piece of equipment being cleaned (e.g., the chestpiece 103 of the stethoscope 101). The readable indicia stores/includes a unique identifier capable of uniquely identifying the piece of equipment (e.g., the stethoscope 101). The readable indicia 116 may be located on the chestpiece 103 of the stethoscope 101. Once inserted into the receiving area 102 of the compliance-based cleaning device 100, the camera may locate and capture the readable indicia 116 and record the unique identifier stored in the readable indicia 116. The camera may include low-light capture functionality, allowing the camera to adequately capture the readable indicia 116 while it is in the receiving area 102.

Figure 6:
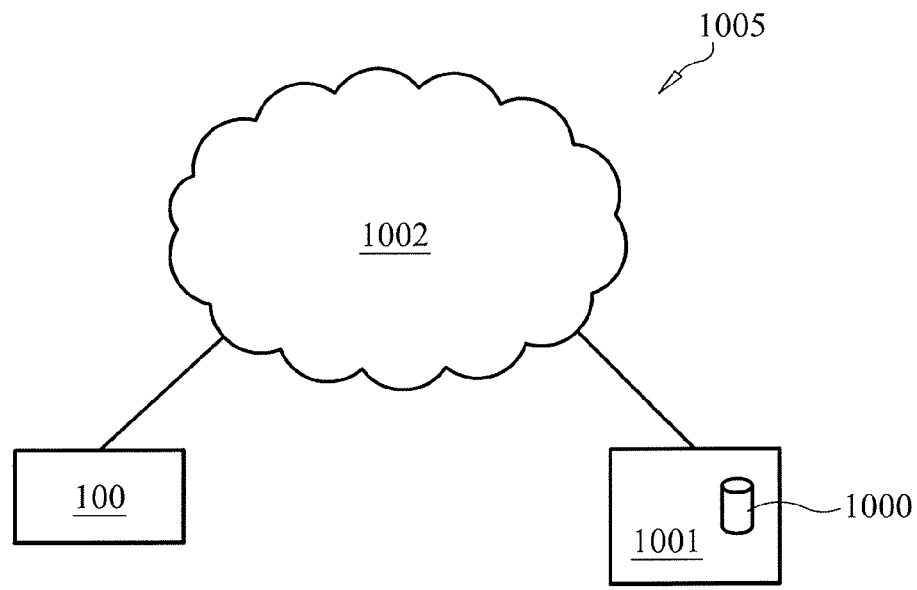
FIG. 6 is a block diagram illustrating a compliance-based cleaning system according to an exemplary embodiment of the present invention.

The readable indicia 116 may be identified using, for example, optical character recognition (OCR). In an exemplary embodiment, OCR may be performed, for example, at the compliance-based cleaning device 100. For example, the compliance-based cleaning device 100 may include a processor 115 that may perform an OCR algorithm. Alternatively, the captured readable indicia 116 may be transmitted as a raw image to a server 1001 (e.g., a server 1001 including the compliance database 1000) that is part of a compliance-based cleaning system 1005, and OCR may be performed at the server 1001. The compliance-based cleaning system 1005 according to an exemplary embodiment of the present invention is shown in FIG. 6.

The identifying information read from the readable indicia 116 may be immediately transmitted to the compliance database 1000 via the network component 111 upon being obtained by the camera. Alternatively, the identifying information read from the readable indicia 116 may be stored in a memory 113 of the compliance-based cleaning device 100 and may later be transmitted to the compliance database 1000. For example, in an exemplary embodiment, each time a piece of equipment (e.g., the chestpiece 103 of a stethoscope 101) is cleaned in the compliance-based cleaning device 100, a cleaning record based on the identifying information read from the readable indicia 116 may be generated by the compliance component 110 and stored in the memory 113. The plurality of stored cleaning records (e.g., cleaning records corresponding to each time a piece of equipment is cleaned in the compliance-based cleaning device 100) may then be transmitted to the compliance database 1000 at a pre-defined time (e.g., all cleaning records may be transmitted to the compliance database 1000 at the end of the day). In an exemplary embodiment, the memory 113 may be utilized to temporarily store cleaning records in the event that the network connection between the compliance-based cleaning device 100 and the compliance database 1000 is not present (e.g., in the event of a network outage).

In an exemplary embodiment, the compliance component 110 includes a radio-frequency identification (RFID) reader such as, for example, a near field communication (NFC) reader, and the readable indicia 116 includes an RFID tag such as, for example, an NFC tag. The NFC tag may be placed on the piece of equipment being cleaned (e.g., the chestpiece 103 of the stethoscope 101), allowing for equipment that does not otherwise include readable 116 indicia such as a serial number, a registration number, a barcode, etc. to be identified by the compliance component 110. Once the NFC tag is read by the NFC reader, a cleaning record(s) based on identifying information stored in the NFC tag may be utilized in a similar manner as described above.

As described above, the compliance database 1000 stores a plurality of cleaning records. The cleaning records may include a plurality of different types of identifying information, resulting in the formation of a robust database that promotes compliance and establishes a record of compliance and non-compliance. For example, as described above, when a cleaning process is performed on a piece of equipment (e.g., a stethoscope 101), compliance data is created. The compliance data includes identifying information obtained by the compliance component 110 of the compliance-based cleaning device 100. This identifying information may be used to create the cleaning records stored in the compliance database 1000.

Identifying information obtained by the compliance component 110 and stored in the cleaning records in the compliance database 1000 may include, for example, (i) identifying information that identifies the piece of equipment (e.g., the stethoscope 101) that has been cleaned, (ii) identifying information that identifies the compliance-based cleaning device 100 used to perform the cleaning, and/or (iii) identifying information that identifies the medical practitioner that performed the cleaning. The cleaning records may further include information identifying, for example, a time at which a cleaning process was performed, or identifying information that indicates whether the medical practitioner sanitized his or her hands at substantially the same time that the piece of equipment was cleaned (e.g., at exactly the same time, or within a short amount of time that is long enough to clean both the piece of equipment and the medical practitioner's hands), as described in further detail below. The identifying information relating to the medical practitioner may be obtained using, for example, an identification camera 117 and/or a scanner 118. The scanner 118 may include, for example, a fingerprint scanner and/or an identification card scanner included as part of the compliance component 110, as described in further detail below.

According to an exemplary embodiment, each cleaning record stored in the compliance database 1000 includes a plurality of pieces of identifying information. For example, each cleaning record may include identifying information corresponding to a unique identifier indicating the compliance-based cleaning device 100 used for that particular cleaning process. For example, a location such as a hospital may utilize a plurality of compliance-based cleaning devices 100 located throughout the hospital, and each compliance-based cleaning device 100 may have a unique identifier, allowing the hospital to determine which compliance-based cleaning devices 100 performed which cleaning processes. Each cleaning record may further include identifying information corresponding to a unique identifier indicating the piece of equipment (e.g., the stethoscope 101) cleaned during that particular cleaning process. This unique identifier may be included in the readable indicia 116 of the stethoscope 101, as described above. Each cleaning record may further include identifying information corresponding to a unique identifier indicating a medical practitioner that performed the cleaning. According to exemplary embodiments, each cleaning record may include additional pieces of identifying information such as, for example, a unique identifier indicating a medical practitioner to whom the corresponding compliance-based cleaning device 100 is assigned/registered, a primary location (e.g., a hospital) at which the corresponding compliance-based cleaning device 100 is located, and a secondary location (e.g., a room in a hospital identified by, for example, a room number) at which the corresponding compliance-based cleaning device 100 is located.

Utilization of the compliance-based cleaning device 100 allows for entities (e.g., hospitals, other medical institutions, insurance companies, government agencies, etc.) to implement forced compliance relating to the cleaning of equipment/tools/devices (e.g., stethoscopes 101). For example, although the regular cleaning of stethoscopes 101 is typically suggested/required in order to prevent the spread of germs, bacteria, viruses, fungus, etc. among patients, medical practitioners using a stethoscope often do not comply with such cleaning suggestions/requirements. As a result, patients on which a stethoscope 101 is used may be unnecessarily exposed to germs, bacteria, viruses, fungus, etc., and thus, may risk contracting sicknesses or diseases, which could have potentially been avoided had the stethoscope 101 used on the patients been properly cleaned. Through the use of the compliance-based cleaning device 100 according to exemplary embodiments of the present invention, compliance and non-compliance relating to cleaning may be accurately tracked, verified and documented, improving cleaning compliance and establishing records for institutional, hospital, facility, office, governmental and other action in the face of non-compliance. In addition to a database of compliance and non-compliance, exemplary embodiments of the present invention allow for entries directly into a patient's electronic medical records (EMRs) and allows for documentary support for billing, consistent with existing and developing requirements of commercial insurers and governmental payors.

In an exemplary embodiment, an entity (e.g., a hospital) may choose to register every piece of equipment (e.g., every stethoscope 101) for which forced compliance is to be implemented that belongs to the hospital in the compliance database 1000. For convenience of description, this entity will be described herein as a hospital, however, it is to be understood that the entity is not limited thereto. For example, the entity may be a doctor's office, an ambulatory surgery center, a nursing facility, a rehabilitation facility, another medical institution, an insurance company, a government agency, etc. The compliance database 1000 may be managed by a third party entity or by the hospital itself. Thus, the compliance database 1000 may be located at the hospital, or at a location remote from the hospital (e.g., at a location managed by the third party entity). Interplay between the compliance-based cleaning device 100 and the compliance database 1000 may be functionally the same regardless of the location of the compliance database 1000. Alternatively, the hospital may choose to register every stethoscope 101 belonging to the hospital to a location in the hospital, such as to a specific room in the hospital. Registering every stethoscope 101 in the hospital in the compliance database 1000 allows for cleaning processes relating to each stethoscope 101 to be accurately tracked.

As described above, in addition to cleaning records including information indicating the tool/equipment/device (e.g., the stethoscope 101) that has been cleaned and information indicating the compliance-based cleaning device 100 used to perform the cleaning, cleaning records may further include information indicating the owner or user (e.g., the medical practitioner) that is associated with a specific tool/equipment/device (e.g., the stethoscope 101) or performed the cleaning. The identifying information indicating the medical practitioner that is associated with or performed the cleaning may be obtained in a variety of manners.

For example, in an exemplary embodiment, the compliance component 110 may include an identification camera 117. Each time a cleaning process is performed by the compliance-based cleaning device 100, the identification camera 117 may capture an image of the medical practitioner that performed the cleaning process. The identification camera 117 may include pan/tilt/zoom functionality, and may automatically identify the position and pose of the medical practitioner's face. The captured image may be stored in the compliance database 1000 and linked to the identifying information indicating the piece of equipment (e.g., the stethoscope 101) that was cleaned and/or the compliance-based cleaning device 100 that performed the cleaning. The medical practitioner also may be identified using, for example, a fingerprint scanner included as a part of the compliance component 110, or an identification card scanner (e.g., a barcode scanner, a camera, an RFID reader, etc.) included as a part of the compliance component 110 that is configured to read the medical practitioner's identification card/badge. The fingerprint scanner and the identification card scanner may be combined into a single component (e.g., the scanner 118 shown in FIG. 1), or they may be separate components.

According to exemplary embodiments, the compliance database 1000 may store a plurality of reference records corresponding to the plurality of pieces of identifying information collected by the compliance-based cleaning device 100. The reference records may be registered by the entity that manages the compliance database 1000 (e.g., a hospital or a third party entity, as described above). Identifying information collected by the compliance-based cleaning device 100 may be compared to corresponding reference records stored in the compliance database 1000 for identification purposes.

For example, a picture of each medical practitioner working in a hospital may be stored in the compliance database 1000 as reference records. When a cleaning process is performed and a picture of the medical practitioner is captured, as described above, the captured picture may be transmitted to the compliance database 1000 and compared to the reference records to identify the medical practitioner that performed the cleaning process. Various types of image/facial recognition algorithms may be utilized to identify the medical practitioner. A similar process of utilizing reference records to perform a comparison and identification operation may be used for other types of identifying information collected by the compliance-based cleaning device 100.

Exemplary embodiments may not utilize reference records and/or image/facial recognition algorithms. These exemplary embodiments may still capture a picture of medical practitioners as cleaning processes are performed. In these exemplary embodiments, the images captured may be stored in the compliance database 1000 without performing a comparison operation, and may be utilized to identify a medical practitioner as needed to, for example, support compliance, billing activities, etc., by referring to the stored records as needed.

Exemplary embodiments that utilize identifying information indicating the medical practitioner that performed a cleaning process may implement a notification system to transmit notifications to the medical practitioners. For example, in exemplary embodiments in which reference records corresponding to medical practitioners are stored in the compliance database 1000, contact information associated with each medical practitioner may also be stored. This contact information may include, for example, a medical practitioner's email address, phone number, pager number, address, etc. A notification may be transmitted from the compliance-based cleaning system 1005 to the medical practitioner upon the occurrence of certain events. Notifications may correspond to warnings issued to medical practitioners. For example, a notification may be sent when a medical practitioner has not cleaned a piece of equipment (e.g., a stethoscope 101) registered to the medical practitioner within a predefined amount of time, when the medical practitioner is in danger of being disciplined for non-compliance, etc. The notifications may be, for example, an email, a phone call, a text, a letter, etc., and records of the notifications may be kept in the compliance database 1000. The notifications may also be transmitted to entities other than the medical practitioners such as, for example, an infection control department in a hospital, a third party entity, a government agency, etc.

The compliance-based cleaning device 100 may include a variety of physical configurations according to exemplary embodiments of the present invention.

Figure 4A:
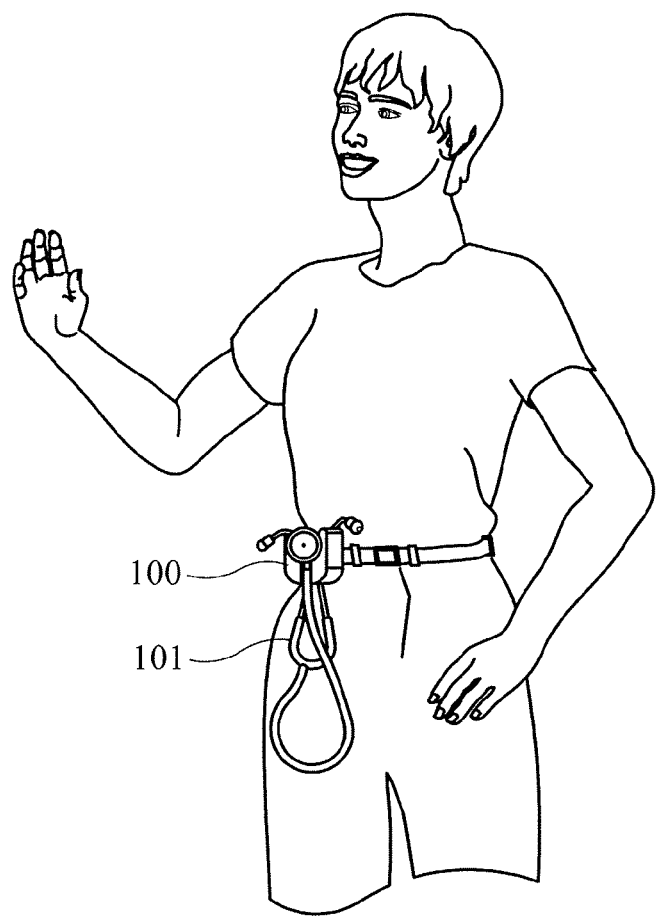
FIGS. 4A-4B show a compliance-based cleaning device that utilizes a belt clip according to an exemplary embodiment of the present invention.
Figure 4B:
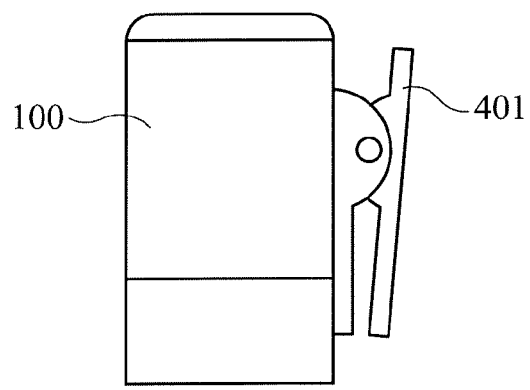

In an exemplary embodiment, the compliance-based cleaning device 100 may be a portable freestanding unit. The portable freestanding compliance-based cleaning device 100 may be easily transported between locations. Alternatively, the compliance-based cleaning device 100 may include attachment means such as, for example, a holster or belt clip 401, as shown in FIGS. 4A-4B, allowing the device 100 to be carried by the medical practitioner. Alternatively, the compliance-based cleaning device 100 may be mounted to a surface such as, for example, a table, desk, wall, etc. The device 100 may include a battery 120 (e.g., a rechargeable battery) and/or may receive power via a standard electrical outlet connection.

Figure 1E:
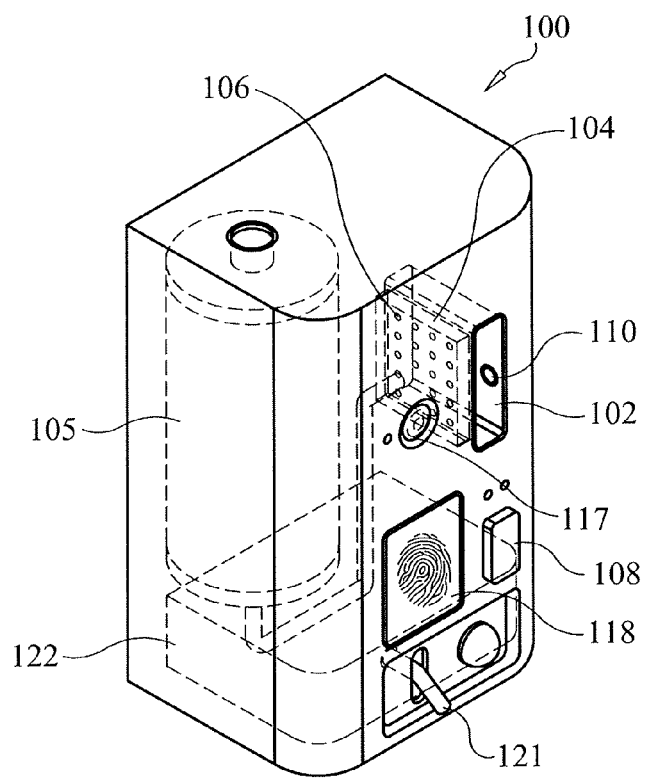
FIG. 1E show a compliance-based cleaning device including a hand sanitizing component according to an exemplary embodiment of the present invention.

FIG. 1E show a compliance-based cleaning device including a hand sanitizing component according to an exemplary embodiment of the present invention.

Referring to FIG. 1E, according to an exemplary embodiment of the present invention, the compliance-based cleaning device 100 further includes a hand sanitizing component 121. As described above, the chestpiece 103 of the stethoscope 101 and a medical practitioner's hands are typically the two greatest causes of the spread of germs, bacteria, viruses, fungus, etc. Inclusion of the hand sanitizing component 121 in the compliance-based cleaning device 100 promotes regular hand cleaning in addition to the cleaning of the piece of equipment (e.g., the stethoscope 101). In an exemplary embodiment, when the medical practitioner inserts the piece of equipment (e.g., the chestpiece 103 of the stethoscope 101) into the receiving area 102 of the compliance-based cleaning device 100, the medical practitioner also places his or her hand(s) in proximity to the hand sanitizing component 121. The hand sanitizing component 121 is connected to a hand sanitizing solution chamber 122 that stores a hand sanitizing solution. The hand sanitizing solution may be, for example, a hand sanitizing gel, an alcohol solution (e.g., about 70% isopropyl alcohol), etc. The hand sanitizing solution may be dispersed automatically in response to the medical practitioner inserting his or her hands into the hand sanitizing component 121 through the use of a sensor similar to the compliance sensor 107, or may be manually dispersed in response to the medical practitioner pressing a button, lever, switch, etc.

In exemplary embodiments that include the hand sanitizing component 121, the compliance data transmitted to the compliance database 1000 may include identifying information indicating whether the medical practitioner sanitized his or her hands. The identification camera 117 and/or the scanner 118 (e.g., a fingerprint scanner and/or an identification card scanner) may be utilized in conjunction with the hand sanitizing component 121 to identify the medical practitioner. Including the hand sanitizing component 121 in the same device (e.g., the compliance-based cleaning device 100) that cleans the piece of equipment (e.g., the stethoscope 101) provides a reminder to the medical practitioner to clean his or her hands every time he or she cleans the piece of equipment. Further, including the hand sanitizing component 121 in the compliance-based cleaning device 100 provides a verifiable and documented process to monitor and track the cleaning of a medical practitioner's hands and the piece of equipment being cleaned together in one efficient, verifiable, documented compliance-based process.

It is to be understood that the hand sanitizing component 121 and hand sanitizing solution chamber 122 shown in FIG. 1E may also be included in the compliance-based cleaning device 100 of FIGS. 1A-1D.

In an exemplary embodiment, rather than transmitting the compliance data from the compliance-based cleaning device 100 to the compliance database 1000, the compliance data may be stored in the memory 113 of the compliance-based cleaning device 100 and manually retrieved at a later time.

FIG. 5 is a block diagram illustrating a compliance-based cleaning device 100 according to an exemplary embodiment of the present invention. The compliance-based cleaning device 100 according to exemplary embodiments may include all or some of the components shown in FIG. 5 and described above. The components of the compliance-based cleaning device are connected to one another via a bus 1006.

FIG. 6 is a block diagram illustrating a compliance-based cleaning system 1005 according to an exemplary embodiment of the present invention.

Referring to FIG. 6, the compliance-based cleaning device 100 communicates with the server 1001, which includes the compliance database 1000, via a network connection 1002 (e.g., an Internet connection, an intranet connection, etc.).

Figure 7:
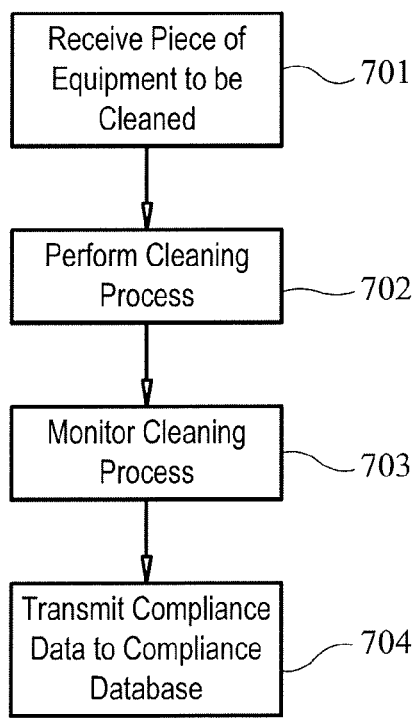
FIG. 7 is a flowchart showing a method of compliance-based cleaning according to an exemplary embodiment of the present invention.

FIG. 7 is a flowchart showing a method of compliance-based cleaning according to an exemplary embodiment of the present invention.

Referring to FIG. 7, at block 701, a piece of equipment (e.g., the stethoscope 101) to be cleaned in the compliance-based cleaning device 100 is received. At block 702, a cleaning process is performed on the piece of equipment upon receiving the piece of equipment in the compliance-based cleaning device 100. At block 703, the cleaning process performed on the piece of equipment is monitored. At block 704, compliance data is transmitted from the compliance-based cleaning device 100 to the compliance database 1000 in response to performing the cleaning process on the piece of equipment. The compliance data includes identifying information obtained during the cleaning process. The identifying information may include, for example, first identifying information that identifies the piece of equipment, second identifying information that identifies the compliance-based cleaning device 100, and third identifying information that identifies a user (e.g., a medical practitioner) that performed the cleaning process on the piece of equipment using the compliance-based cleaning device 100.

Exemplary embodiments of the present invention may be utilized with a variety of stethoscopes. For example, exemplary embodiments may be utilized with stethoscopes having dual-head chestpieces including a diaphragm on one side and a bell on the other side, single-head chestpieces including both the diaphragm and bell on one side, acoustic stethoscopes, electronic stethoscopes, etc. Exemplary embodiments may be utilized with stethoscopes made by a variety of manufacturers including, for example, stethoscopes made by 3M (e.g., the 3M LITTMAN stethoscope), WELCH ALLYN, etc.

Having described exemplary embodiments for a compliance-based cleaning device, system and method, it is noted that modifications and variations can be made by persons skilled in the art in light of the above teachings. It is therefore to be understood that changes may be made in exemplary embodiments of the invention, which are within the scope and spirit of the invention as defined by the appended claims. Having thus described the invention with the details and particularity required by the patent laws, what is claimed and desired protected by Letters Patent is set forth in the appended claims.

What is claimed is:

1. A compliance-based cleaning device, comprising:
a receiving area configured to receive a piece of equipment to be cleaned, wherein the piece of equipment comprises a stethoscope, and the receiving area comprises:
a substantially enclosed box having an opening on one side,
wherein the opening is accessible from a front side of the compliance-based cleaning device, the box is shaped and dimensioned to receive a bell and a diaphragm of the stethoscope through the opening, and the bell and the diaphragm are inserted into the box through the opening in a substantially horizontal direction extending from the front side of the compliance-based cleaning device toward an opposing rear side of the compliance-based cleaning device;
a cleaning member located in proximity to the receiving area and configured to perform a cleaning process on the piece of equipment;
a compliance component configured to monitor the cleaning process performed on the piece of equipment; and
a network component configured to transmit compliance data to a compliance database in response to the cleaning member performing the cleaning process on the piece of equipment, wherein the compliance data includes identifying information obtained by the compliance component.

2. The compliance-based cleaning device of claim 1, wherein the compliance component comprises a camera configured to capture a readable indicia disposed on the piece of equipment, wherein the readable indicia uniquely identifies the piece of equipment.

3. The compliance-based cleaning device of claim 2, wherein the readable indicia comprises at least one of a serial number, a registration number, and a barcode.

4. The compliance-based cleaning device of claim 1, wherein the cleaning process comprises disinfecting the piece of equipment.

5. The compliance-based cleaning device of claim 1, wherein the cleaning process comprises sterilizing the piece of equipment.

6. The compliance-based cleaning device of claim 1, further comprising:
a cleaning solution chamber connected to the cleaning member and configured to store a liquid cleaning solution and provide the liquid cleaning solution to the cleaning member,
wherein the cleaning process is performed on the piece of equipment using the liquid cleaning solution.

7. The compliance-based cleaning device of claim 6, wherein the cleaning member comprises a plurality of holes, and the liquid cleaning solution is sprayed onto the piece of equipment through the plurality of holes during the cleaning process.

8. The compliance-based cleaning device of claim 1, further comprising:
a compliance sensor disposed in the receiving area, wherein the compliance sensor is configured to detect insertion of the piece of equipment in the receiving area.

9. The compliance-based cleaning device of claim 8, wherein the cleaning process is automatically started upon the compliance sensor detecting insertion of the piece of equipment in the receiving area.

10. The compliance-based cleaning device of claim 1, further comprising:
a hand sanitizing solution chamber configured to store a hand sanitizing solution; and
a hand sanitizing component connected to the hand sanitizing solution chamber and configured to sanitize a hand of a user performing the cleaning process, wherein the identifying information indicates whether the user performed a hand sanitization cleaning process at substantially a same time as the cleaning process is performed on the piece of equipment.

11. The compliance-based cleaning device of claim 1, wherein the identifying information includes first identifying information that identifies the piece of equipment.

12. The compliance-based cleaning device of claim 11, wherein the identifying information includes second identifying information that identifies the compliance-based cleaning device.

13. The compliance-based cleaning device of claim 12, wherein the identifying information includes third identifying information that identifies a user that performed the cleaning process on the piece of equipment using the compliance-based cleaning device.

14. The compliance-based cleaning device of claim 13, wherein the identifying information includes fourth identifying information that indicates whether the user performed a hand sanitization cleaning process at substantially a same time that the cleaning process is performed on the piece of equipment.

* * * * *